United States Patent [19]

Reeve

[11] Patent Number: 5,342,836
[45] Date of Patent: Aug. 30, 1994

[54] NITROGEN-BASED STABILIZERS FOR 3-ISOTHIAZOLONES

[75] Inventor: Paul F. D. Reeve, Le Plan de Grasse, France

[73] Assignee: Rohm and Haas Company, Philadelphia, Pa.

[21] Appl. No.: 929,899

[22] Filed: Aug. 11, 1992

[51] Int. Cl.$^5$ .................. A01N 43/36; A01N 43/38; C07D 275/02
[52] U.S. Cl. .................. 514/242; 514/338; 514/342; 514/372; 514/373; 548/206; 548/207; 548/214
[58] Field of Search .............. 514/372, 373, 242, 338, 514/342; 548/206, 207, 214

[56] References Cited

U.S. PATENT DOCUMENTS

| | | | |
|---|---|---|---|
| 3,523,121 | 8/1970 | Lewis et al. | 260/306.7 |
| 3,761,488 | 9/1973 | Lewis et al. | 260/302 |
| 3,870,795 | 3/1975 | Miller et al. | 424/270 |
| 4,067,878 | 1/1978 | Miller et al. | 260/302 A |
| 4,129,448 | 12/1978 | Greenfield et al. | 106/15 R |
| 4,150,026 | 4/1979 | Miller et al. | 260/299 |
| 4,165,318 | 8/1979 | Greenfield et al. | 260/302 A |
| 4,173,643 | 11/1979 | Law . | |
| 4,241,214 | 12/1980 | Miller et al. | 548/101 |
| 4,396,413 | 8/1983 | Miller et al. . | |
| 4,906,274 | 3/1990 | Mattox et al. | 71/67 |
| 5,127,934 | 7/1992 | Mattox et al. | 71/67 |

FOREIGN PATENT DOCUMENTS

| | | |
|---|---|---|
| 332336 | 3/1989 | European Pat. Off. . |
| 2008846 | 2/1988 | United Kingdom . |
| 435439 | 11/1990 | United Kingdom . |
| 443821 | 8/1991 | United Kingdom . |

OTHER PUBLICATIONS

"Kathon ® 886MW Microbicide & Kathon ® 893MW Fungicide: Analysis in Metalworking Fluids by High-Performance Liquid Chromatography" 1988, R&H Co.

Japanese Patents Gazette (Section CH, Wk 35, 11 Oct. 1978 Abstract 62762A).
Chemical Patents Index (Section CH, Wk 9042, 12 Dec. 1990 Abstract 90-3/8326/42).
Chemical Abstracts (vol. 79, No. 13, 1 Oct. 1973 Abstract 74918h).

*Primary Examiner*—Robert W. Ramsuer
*Assistant Examiner*—Jacqueline Haley
*Attorney, Agent, or Firm*—Michael B. Fein

[57] ABSTRACT

A method of protecting 3-isothiazolones of the formula:

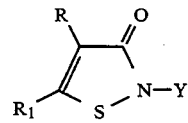

wherein

Y is $(C_1-C_{18})$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylthio, arylthio, haloalkoxy, cycloaklylamino, carbamoxy, or isothiazolonyl; an unsubstituted or halo-substituted $(C_2-C_8)$alkenyl or alkynyl; a $(C_7-C_{10})$aralkyl optionally substituted with one or more of halogen, $(C_1-C_4)$alkyl or $(C_1-C_4)$alkoxy; and an aryl optionally substituted with one or more of halogen, nitro, $(C_1-C_4)$alkyl, $(C_1-C_4)$alkylacylamino, carb$(C_1-C_4)$alkoxy or sulfamyl; and R and R$^1$ is each independently H, halogen $(C_1-C_4)$alkyl, $(C_4-C_8)$ cycloalkyl or joined together to form a phenyl; comprising incorporating therewith an effective amount of a nitrogen-containing, sulphur-free compound, capable of reversibly associating with said isothiazolone.

The compounds and compositions are also described.

7 Claims, No Drawings

NITROGEN-BASED STABILIZERS FOR 3-ISOTHIAZOLONES

This invention concerns the stabilization of 3-isothiazolone compounds, particularly in metal working fluid concentrates, by the incorporation with those compounds of certain nitrogen-based compounds.

Isothiazolones are of significant commercial value as microbicides to prevent spoilage of certain aqueous and non-aqueous products caused by microorganisms. They are highly effective microbicides (as used herein, "microbicides" includes bactericides, fungicides and algicides, and microbicidal activity is intended to include both the elimination of and the inhibition or prevention of growth of microbial organisms such as bacteria, fungi and algae). By suitable choice of functional groups, they are useful in a broad range of applications.

One significant area of application for isothiazolones is as microbicides in metal working fluids. Metal working fluids are proprietary combinations of chemicals which may contain, inter alia, ingredients such as alkanolamines, petroleum sulfonate surfactants, oils (naphthenic, paraffinic, etc), chlorinated paraffins and fatty esters, sulfurized fatty compounds, phosphate esters, fatty acids and their amine salts, glycols, polyglycols, boric acid esters and amides. They are utilized in the milling, machining, drilling, and other processing technologies for fabricating metal for the purposes of lubricating, cooling, preventing surface corrosion, and the like. They are sold in the form of active metal working fluid (MWF) concentrates, and are diluted in use to 1-10% active ingredient in water.

Because metal working fluids are recycled and stored, the growth of microorganisms is favored. Isothiazolones have been found effective in preventing the growth of such organisms. However, certain components in the metal working fluids tend to destroy the isothiazolone and so remove its microbicidal protective activity. This is a particular problem when the MWFs are in concentrate form. It has been found that even some other microbicides, present in combination with isothiazolones, may attack the isothiazolones. An example of this is the sodium salt of 2-mercapto pyridine-N-oxide (sodium omadine), which has been found to remove 5-chloro-2-methyl isothiazolone from any system in which the two are present together.

Indeed, generally, it has long been recognized that either in storage prior to addition to a substrate to be treated or after addition, the efficacy of isothiazolones in many environments may be decreased because they are not stable under practical conditions of long term storage. Means have thus been sought for some time to improve the stability of isothiazolones.

U.S. Pat. Nos. 3,870,795 and 4,067,878 teach the stabilization of isothiazolones against chemical decomposition by addition of a metal nitrite or metal nitrate, but teach that other common metal salts, including carbonates, sulfates, chlorates, perchlorates, and chlorides are ineffective in stabilizing solutions of isothiazolones, such solutions usually being in water or in an hydroxylic solvent. U.S. Pat. No. 4,150,026 and U.S. Pat. No. 4,241,214 teach that metal salt complexes of isothiazolones are useful because they have enhanced thermal stability, while retaining biological activity.

It is known to use certain organic stabilizers for isothiazolones, generally for use situations where metal salts may create problems, such as corrosion, coagulation of latices, insolubility in non-aqueous media, interaction with the substrate to be stabilized, and the like. Formaldehyde or formaldehyde-releasing chemicals are known as stabilizers, (see U.S. Pat. Nos. 4,165,318 and 4,129,448), as are certain organic chemicals such as orthoesters (EP-A-315,464), epoxides (EP-A-342,852), and carbonyl compounds (EP-A-435439).

EP-A-443821 discloses stabilizers for isothiazolones characterized in that they are sulphur-containing, and are capable of reversibly associating with isothiazolones.

We have now discovered a further class of compounds which provide considerable and surprising stability to isothiazolones against decomposition, particularly in MWF concentrates. In its broadest aspect the invention provides a method of protecting against chemical degradation an isothiazolone of the formula:

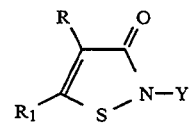

wherein Y is $(C_1-C_{18})$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylthio, arylthio, haloalkoxy, cycloalkylamino, carbamoxy, or isothiazolonyl; an unsubstituted or halo-substituted $(C_2-C_8)$alkenyl or alkynyl; a $(C_7-C_{10})$aralkyl optionally substituted with one or more of halogen, $(C_1-C_4)$alkyl or $(C_1-C_4)$alkoxy; or an aryl optionally substituted with one or more of halogen, nitro, $(C_1-C_4)$alkyl, $(C_1-C_4)$alkyl-acylamino, carb$(C_1-C_4)$alkoxy or sulfamyl; and $R_1$ and R are each independently H, halogen, $(C_1-C_4)$alkyl, $(C_4-C_8)$ cycloalkyl or joined to form a phenyl; comprising incorporating therewith an effective amount of a nitrogen-containing, sulphur-free compound, capable of reversibly forming an adduct with said isothiazolone. The precise nature of the association between the nitrogen containing compounds of the present invention and isothiazolones is not yet fully understood. It is believed that hydrogen-bonding may play a role, although the invention is of course not limited to such a case. The entity resulting from this association is hereinafter referred to as the 'association product'.

The association product is generally hydrolysable, and thus the association process may be reversed by hydrolysis, usually accomplished through dilution.

The invention provides a particularly advantageous form of protection, or stabilization. These stabilizers can be used to 'lock up' an isothiazolone, in the form of a stable association product which is resistant to chemical degradation, and then when desired they can be made to 'release' the isothiazolone by reversing the process of association—usually simply by dilution of the product. Accordingly another aspect of the invention provides a compound comprising an association product of an isothiazolone as defined above and a nitrogen-containing, sulphur-free compound, wherein said association product may be decomposed to release said isothiazolone. Preferably the association product may be hydrolysed to release the isothiazolone.

In another aspect the invention provides a composition comprising an isothiazolone as defined above, a nitrogen-containing, sulphur-free compound as defined above, and optionally a solvent. In a further aspect the invention comprises the use of a nitrogen-containing, sulphur-free compound as previously defined to protect an isothiazolone against chemical degradation.

The invention has particular value in the field of metal working fluids, which are commonly stored in concentrate form. Some of the components in MWFs are extremely aggressive towards isothiazolones when in concentrate form, but of little threat when diluted to the normal use dilution. Thus the present invention can be employed by adding a stabilizer to protect the isothiazolones in the concentrate, the isothiazolone then being released automatically upon dilution by hydrolysis of the isothiazolone-stabilizer association.

The isothiazolones which are stabilized include those disclosed in U.S. Pat. Nos. 3,523,121 and 3,761,488 and represented by the formula:

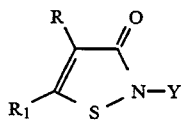

as defined above.

Preferred substituents for Y are substituted or unsubstituted ($C_1$–$C_{18}$) alkyl or ($C_3$–$C_{12}$) cycloalkyl; R is preferred to be H, or Me; and $R^1$ is preferred to be H. Representative of such preferred Y substituents are methyl, ethyl, propyl, isopropyl, butyl, hexyl, octyl, cyclohexyl, benzyl, 3,4-dichlorobenzyl, 4-methoxybenzyl, 4-chlorobenzyl, 3,4-dichlorophenyl, 4-methoxyphenyl, hydroxymethyl, chloromethyl, chloropropyl, hydrogen, and the like.

Particularly preferred isothiazolones are 2-methyl-3-isothiazolone, and 2-n-octyl-3-isothiazolone.

The stabilizers are naturally almost always organic compounds. Preferred stabilizers include nitrogen-based heterocycles, such as pyridine-N-oxide, and in particular pyridine, 2-pyrrolidone and 1-methyl 2-pyrrolidone. Also preferred is s-triazine and particularly dimethyl oxime.

In order for protection of the isothiazolone to be effective, the molar ratio of stabilizer to isothiazolone should preferably be at least 0.1:1, and most preferably at least 0.5:1. The minimum ratio generally depends on the aggressiveness of the system in which the isothiazolone is contained. A typical preferred range is from 0.5:1 to 1.5:1. However, some of the compounds which act as stabilizers may find other uses in the systems to which isothiazolones have been added—e.g., as microbicides in their own right. In such cases, stabilizer: isothiazolone molar ratios may be greater than 10:1.

Compositions of isothiazolone and stabilizer may additionally contain solvents. A suitable solvent will be any organic solvent which dissolves the isothiazolone, is compatible with the proposed end use, does not destabilize the isothiazolone, and does not react with the stabilizer to prevent its protective action.

Hydroxylic solvents, for example, polyols, such as glycols, alcohols and the like, may be used. In certain formulations, hydrocarbons, either aliphatic or aromatic, are useful solvents.

Preferred solvents are capped polyols, wherein the free hydroxyl group is replaced with an ether or ester function. Especially preferred are 2,5,8,11-tetraoxadodecane, commonly known as triethylene glycol dimethyl ether, and 4,7-dioxaundecanol-1 acetate, commonly known as diethylene glycol butyl ether acetate.

Water is a solvent for certain of the preferred isothiazolones and, the stabilizer may be employed in aqueous formulations.

In certain cases the association products formed according to the invention may be in the form of a solid precipitate. This can generally be avoided by standard techniques for increasing the solubility product of a system such as adding emulsifiers, or diluting the system. Those skilled in the art will have little difficulty in altering the conditions to avoid precipitate formation if that should be a problem in any particular case.

It is known in the art that the performance of microbicides may be enhanced by combination with one or more other microbicides. Thus, other known microbicides may be combined advantageously with the compositions or compounds of this invention.

Uses of these protected isothiazolones may be at any locus subject to contamination by bacteria, fungi, yeast or algae. Typical loci are in aqueous systems such as water cooling, laundry rinse water, oil systems such as cutting oils, oil fields and the like where microorganisms need to be killed or where their growth needs to be controlled. However, they may also be used in all applications for which known microbicidal compositions are useful; preferred utilities of the compositions are to protect wood paint, adhesive, glue, paper, textile, leather, plastics, cardboard, lubricants, cosmetics, food, caulking, feed and industrial cooling water from microorganisms.

The following Examples are intended to illustrate the present invention. All percentages are by weight unless otherwise specified. Methods for quantitative determination of the isothiazolones in the following Examples in metal working fluids are described in detail in "Kathon ® 886 MW Microbicide and Kathon ® 893 MW Fungicide: Analysis in Metalworking Fluids by High-Performance Liquid Chromatography", 1988, Rohm and Haas Company.

EXAMPLE 1

This Example illustrates the protection afforded to isothiazolones by the stabilizers of the present invention.

Monoethanolamine is known to degrade most isothiazolones when in contact with them in concentrated form. It is a component of metal working fluids, and is therefore a particular problem when present with isothiazolones in MWF concentrates.

In the following Example, a test system was used which comprised a 1:1 water/propylene glycol solvent, 10% monoethanolamine, 900 ppm of 2n-octyl-3-isothiazolone, and a stabilizer according to the invention. The system was maintained at 25° C., and the concentration of isothiazolone remaining after 1,2,4,8 and 12 weeks respectively was determined. Isothiazolone concentration was determined by removing an aliquot from the system at the appropriate time, diluting it 50-fold with a 1:1 water/propylene glycol solution, and then analyzing for isothiazolone by HPLC.

Referring to Table 1, it should be noted that the initial concentration of isothiazolone in each case was 900 ppm. The subsequent readings are percentages of that value, and are accurate to ±5%.

TABLE 1

| STABILIZER | STABILIZER CONCENTRATION (PPM) | % ISOTHIAZILONE REMAINING (±5%) | | | | |
|---|---|---|---|---|---|---|
| | | 1 WK | 2 WKS | 4 WKS | 8 WKS | 12 WKS |
| None (control) | 0 | 72 | 0 | | | |
| Pyridine | 1000 | 98 | 98 | 98 | 100 | 100 |
| 2-pyrrolidone | 1000 | 97 | 98 | 94 | 94 | 97 |
| 1-methyl-2-pyrrolidone | 1000 | 97 | 96 | 91 | 96 | 98 |
| Dimethyl oxime | 1000 | — | 94 | 92 | 96 | 96 |
| Pyridine-N-oxide | 1000 | 91 | 83 | 67 | 48 (6 wks) | |
| s-triazine | 1000 | 98 | 82 | 59 | 18 | |

Referring to Table 1, it can be seen that with no stabilizer present the isothiazolone is rapidly decomposed by the monoethanolamine, having completely disappeared within two weeks. The present invention is limited to those nitrogen-containing, sulphur-free compounds which are capable of reversibly associating with the isothiazolone. As can be seen from the remaining examples in Table 1, these provide exceptional protection for the isothiazolone. As a general rule, it is considered that useful stabilization is achieved if approximately 80% of the isothiazolone remains after 4 weeks, although when compared with the loss of isothiazolone with no stabilizer present, retention of about 60% isothiazolone after 4 weeks may be considered to be effective stabilization.

I claim:

1. A method of protecting against chemical degradation an isothiazolone of the formula:

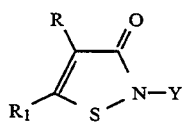

wherein
Y is $(C_1-C_{18})$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylthio, arylthio, haloalkoxy, cycloaklylamino, carbamoxy, or isothiazolonyl; an unsubstituted or halo-substituted $(C_2-C_8)$ alkenyl or alkynyl; a $(C_7-C_{10})$aralkyl optionally substituted with one or more of halogen, $(C_1-C_4)$alkyl or $(C_1-C_4)$alkoxy; or an aryl optionally substituted with one or more of halogen, nitro, $(C_1-C_4)$alkyl, $(C_1-C_4)$alkyl-acylamino, carb$(C_1-C_4)$alkoxy or sulfamyl; and R and $R^1$ are each independently H, halogen, $(C_1-C_4)$alkyl, $(C_4-C_8)$ cycloalkyl or joined together to form a phenyl; comprising incorporating therewith an effective stabilizing amount of a compound selected from the group consisting of s-triazine, dimethyl oxime, pyridine, and pyridine-N-oxide.

2. Method according to claim 1, wherein Y is $(C_1-C_{18})$ alkyl or $(C_3-C_{12})$ cycloalkyl; R is H or Me; and $R^1$ is H.

3. Method according to claim 2 wherein said isothiazolone is 2-methyl-3-isothiazolone or 2-n-octyl-3-isothiazolone.

4. Composition comprising (A) an isothiazolone of formula I,

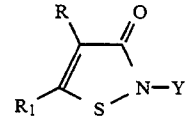

wherein
Y is $(C_1-C_{18})$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylthio, arylthio, haloalkoxy, cycloaklylamino carbamoxy, or isothiazolonyl; an unsubstituted or halo-substituted $(C_2-C_8)$ alkenyl or alkynyl; a $(C_7-C_{10})$aralkyl optionally substituted with one or more of halogen, $(C_1-C_4)$alkyl or $(C_1-C_4)$alkoxy; or an aryl optionally substituted with one or more of halogen, nitro, $(C_1-C_4)$alkyl, $(C_1-C_4)$alkyl-acylamino, carb$(C_1-C_4)$alkoxy or sulfamyl; and R and $R^1$ are each independently H, halogen, $(C_1-C_4)$alkyl, $(C_4-C_8)$cycloalkyl or joined together to form a phenyl; and (B) an amount of a compound selected from the group consisting of a s-triazine, dimethyl oxime, pyridine, and pyridine-N-oxide sufficient to stabilize said isothiazolone.

5. Composition according to claim 4 wherein the molar ratio of said compound to said isothiazolone is at least 0.1:1.

6. Composition according to claim 4 wherein the molar ratio of said compound to said isothiazolone is at least 0.5:1.

7. Composition comprising an association product of an isothiazolone of formula I

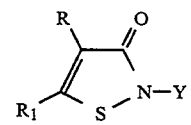

wherein
Y is $(C_1-C_{18})$alkyl or $(C_3-C_{12})$cycloalkyl each optionally substituted with one or more of hydroxy, halo, cyano, alkylamino, dialkylamine, arylamino, carboxy, carbalkoxy, alkoxy, aryloxy, alkylthio, arylthio, haloalkoxy, cycloaklylamino, carbamoxy, or isothiazolonyl; an unsubstituted or halo-substituted $(C_2-C_8)$ alkenyl or alkynyl; a $(C_7-C_{10})$aralkyl optionally substituted with one or more of halogen, $(C_1-C_4)$alkyl or $(C_1-C_4)$alkoxy; or an aryl optionally substituted with one or more of halogen, nitro, $(C_1-C_4)$alkyl, $(C_1-C_4)$alkyl-acylamino, carb$(C_1-C_4)$alkoxy or sulfamyl; and R and $R^1$ are each independently H, halogen, $(C_1-C_4)$alkyl, $(C_4-C_8)$ and a compound selected from the group consisting of s-triazine, dimethyl oxime, pyridine, and pyridine-N-oxide.

* * * * *